(12) United States Patent
Boveja

(10) Patent No.: US 6,269,270 B1
(45) Date of Patent: Jul. 31, 2001

(54) APPARATUS AND METHOD FOR ADJUNCT (ADD-ON) THERAPY OF DEMENTIA AND ALZHEIMER'S DISEASE UTILIZING AN IMPLANTABLE LEAD AND EXTERNAL STIMULATOR

(76) Inventor: Birinder Bob Boveja, 8879 S. Chestnut Hill Way, Highlands Ranch, CO (US) 80126

( * ) Notice: Subject to any disclaimer, the term of this patent is extended or adjusted under 35 U.S.C. 154(b) by 0 days.

(21) Appl. No.: 09/178,057

(22) Filed: Oct. 26, 1998

(51) Int. Cl.[7] .............................................. A61N 1/36
(52) U.S. Cl. ..................................... 607/45; 607/59
(58) Field of Search ............................. 607/45, 46, 2, 607/59, 60

(56) References Cited

U.S. PATENT DOCUMENTS

| | | | |
|---|---|---|---|
| 3,760,812 | 9/1973 | Timm et al. | 128/418 |
| 3,796,221 | 3/1974 | Hagfors | 128/421 |
| 3,817,254 | 6/1974 | Maurer | 128/421 |
| 4,573,481 | 3/1986 | Bullara | 128/784 |
| 4,688,574 * | 8/1987 | Dufresne et al. | 607/59 |
| 4,690,145 * | 9/1987 | King-Smith et al. | 607/63 |
| 4,699,143 * | 10/1987 | Dufresne et al. | 607/46 |
| 4,702,254 | 10/1987 | Zabara | 128/421 |
| 4,867,164 | 9/1989 | Zabara | 128/421 |
| 4,979,511 | 12/1990 | Terry, Jr. | 128/642 |
| 5,025,807 | 6/1991 | Zabara | 128/421 |
| 5,031,618 | 7/1991 | Mullett | 128/421 |
| 5,094,242 | 3/1992 | Gleason et al. | 128/642 |
| 5,269,303 | 12/1993 | Wernicke et al. | 607/45 |
| 5,299,569 * | 4/1994 | Wernicke et al. | 607/45 |
| 5,330,515 | 7/1994 | Rutecki et al. . | |
| 5,540,734 | 7/1996 | Zabara | 607/46 |
| 5,735,887 * | 4/1998 | Barreras, Sr. et al. | 607/60 |
| 5,752,979 | 5/1998 | Benabid | 607/72 |
| 5,938,690 * | 8/1999 | Law et al. | 607/46 |

OTHER PUBLICATIONS

Scherder, E.J.A., A. Bouman and A.M. Steen; Effects of Short–term Transcutaneous Electrical Nerve Stimulation on Memory and Affective Behaviour in Patients With Probable Alzheimer's Disease; Behavioral Brain Research 67 (1995); pp. 211–219.

Scherder, Erik J.A., Anke Bouman and Louis Steen; Influence of Transcutaneous Electrical Nerve Stimulation on Memory in Patients With Dementia of the Alzheimer Type; Journal of Clinical and Experimental Neuropsychology 1992, vol. 14, No. 6, pp. 951–960.

Rutecki, Paul; Anatomical, Physiological, and Theoretical Basis for the Antiepileptic Effect of Vagus Nerve Stimulation; Epilepsia, 31 (Suppl. 2):S1–S6, 1990.

Wilder, B.J., Summary and Conclusions; Epilepsia, 31 (Suppl. 2):S60, 1990.

Hammond, Edward J., Basim M. Uthman, Steven A. Reid, and B.J. Wilder; Electrophysiological Studies of Cervical Vagus Nerve Stimulation in Humans: I. EEG Effects; Epilepsia, 33(6):1013–1020, 1992.

Hammond, Edward J., Basim M. Uthman, Steven A. Reid and B.J. Wilder; Electrophysiologic Studies of Cervical Vagus Nerve Stimulation in Humans: II. Evoked Potentials; Epilepsia, 33(6): 1021–1028.

(List continued on next page.)

*Primary Examiner*—Kennedy Schaetzle
(74) *Attorney, Agent, or Firm*—Sheridan Ross P.C.

(57) ABSTRACT

An apparatus and method for adjunct (add-on) therapy of dementia and Alzheimer's disease comprises an implantable lead-receiver, an external stimulator having controlling circuitry and a power source, and an electrode to inductively couple the stimulator to the lead-receiver. The external stimulator emits electrical pulses to stimulate a cranial nerve such as the left vagus nerve according to a predetermined program selected from at least two predetermined programs.

16 Claims, 15 Drawing Sheets

OTHER PUBLICATIONS

Hornig, Gregory W. MD, Jerome V. Murphy, MD, Gloria Schallert, RN and Christy Tilton RN; Left Vagus Nerve Stimulation in Children With Refractory Epilepsy: An Update; Southern Medical Journal, vol. 90, No. 5; May 1997; pp. 484–488.

Phillips, Pat; Current View of Advances in Epilepsy; JAMA; Sep. 17, 1997; vol. 278, No. 11; pp. 883–886.

Salinsky, Martin C. And Kim J. Burchiel; Vagus Nerve Stimulation Has No Effect on Awake EEG Rhythms in Humans; Epilepsia; 34(2):299–304, 1993.

Takaya, Mikio, Wendy J. Terry and Dean K. Naritoku; Vagus Nerve Stimulation Induces a Sustained Anticonvulsant Effect; Epilepsia; 37(11):1111–1116; 1996.

Reid, Steven A.; Surgical Technique for Implantation of the Neurocybernetic Prosthesis; Epilepsia, 31 (Suppl. 2): S38–S39, 1990.

Labar, Douglas, Blagovest Nikolov, Brent Tarver and Richard Fraser; Vagus Nerve Stimulation for Symptomatic Generalized Epilepsy: A Pilot Study; Epilepsia; 39(2):201–205, 1998.

Ben–Menachem, MD, Ph.D; Vagus Nerve Stimulation for Treatment of Seizures? Yes; Arch Neurol/Vo.. 55, Feb. 1998; pp. 231–234.

McLachlan, Richard S.; Vagus Nerve Stimulation for Intractable Epilepsy: A Review; Journal of Clinical Neurophysiology; 14(5): pp. 358–368.

Fisher, Robert S., MD, Ph.D., Gregory L. Krauss, MD, Eugene Ramsay, MD; Kenneth Laxer, MD and John Gates MD; Assessment of Vagus Nerve Stimulation for Epilepsy: Report of the Therapeutics and Technology Assessment Subcommittee of the American Academy of Neurology; Neurology; 1997; 49:293–297.

* cited by examiner

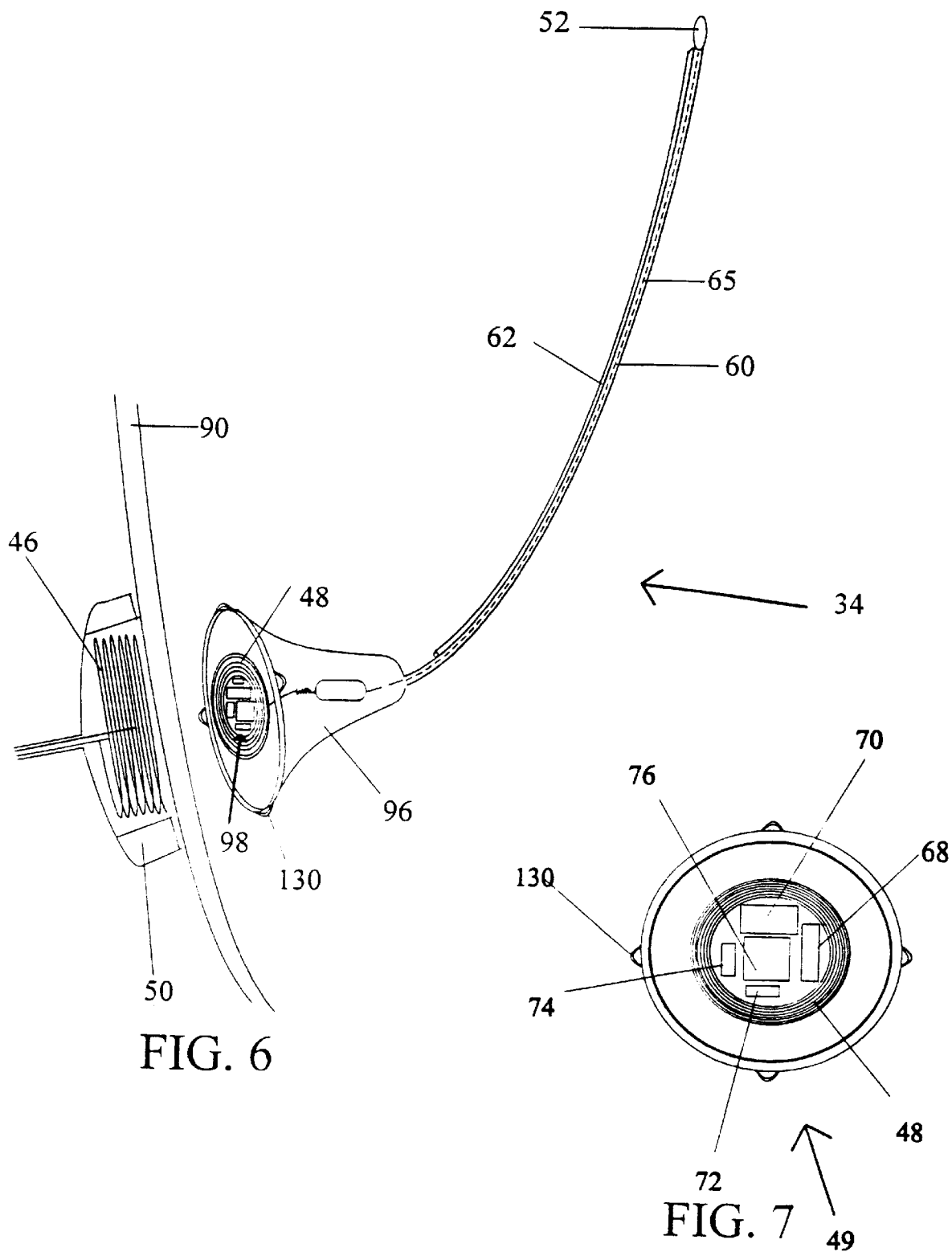

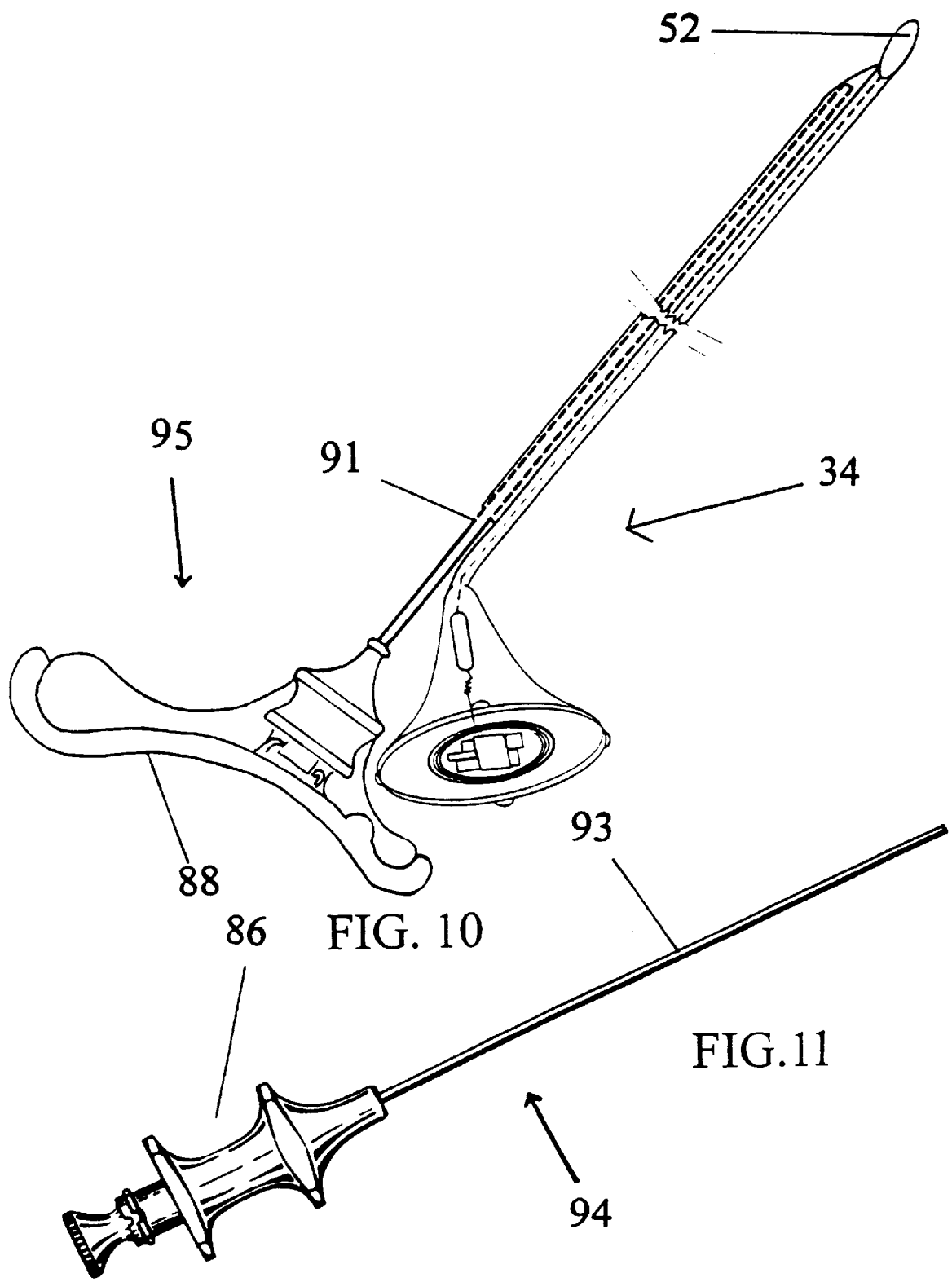

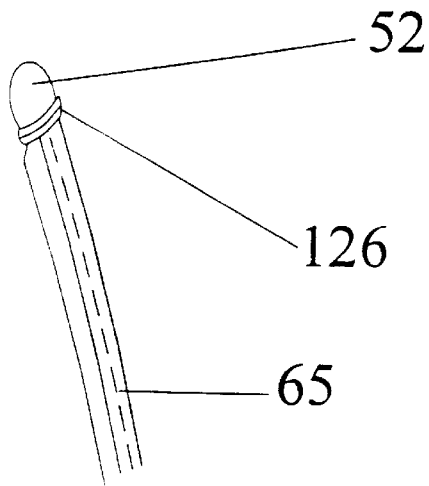
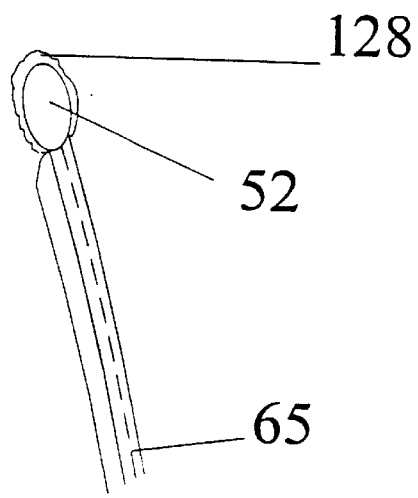
FIG. 21
FIG. 22
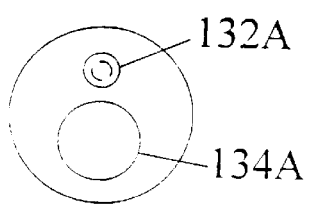
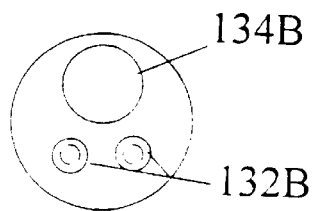
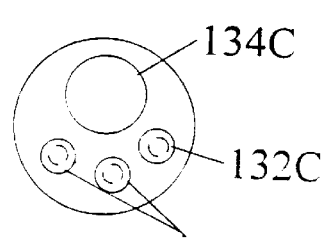
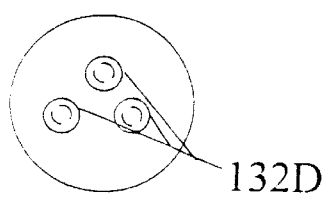
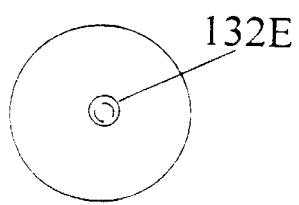
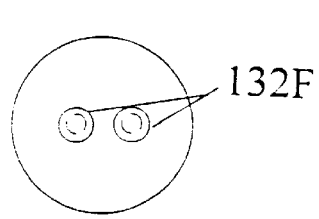
FIG. 23

APPARATUS AND METHOD FOR ADJUNCT (ADD-ON) THERAPY OF DEMENTIA AND ALZHEIMER'S DISEASE UTILIZING AN IMPLANTABLE LEAD AND EXTERNAL STIMULATOR

BACKGROUND

1. Field of Invention

This invention relates generally to non-pharmacologic adjunct (add-on) treatment for Dementia, more specifically to adjunct treatment of Dementia including Alzheimer's disease by modulating electrical signals to a selected nerve or nerve bundle utilizing an easily implanted lead-receiver and an external stimulator.

2. Background

There is mounting scientific evidence that electrical stimulation has beneficial therapeutic effects for patients with Dementia and probable Alzheimer's disease. Most of the scientific studies are performed utilizing the technique of transcutaneous electrical nerve stimulation (TENS). In the TENS method (such as a device manufactured by Xytron Medical), two standard carbon rubber electrodes with gel are fixed on patient's skin across the tissue to be stimulated, one electrode being the negative pole and other being the positive pole. Utilizing the two electrodes, asymmetric biphasic pulses are used for stimulation with varying frequency and pulse widths. Because the skin has high impedance, relatively large outputs are required to stimulate, and the site to be stimulated is not very specific. Other tissues including muscle, between the two skin electrodes will be stimulated.

Another method of stimulating nerve is to use a percutaneous needle, or a lead with one end (distal end) being next to the nerve and utilizing a patch somewhere on the skin as the return electrode. Such a method is not feasible for long term stimulation because of the potential for infection, but can be useful for short term testing.

Two recent studies reported by Scherder et al., using TENS as the method of stimulation, described the benefits on memory and affective behavior in patients with probable Alzheimer's disease. There was a partial disappearance of the treatment effects on memory and affective behavior after a treatment-free period of 6 weeks, suggesting that continuation of the stimulation is necessary for maintaining or even further improving the treatment effects.

The rationale underlying the TENS study was that peripheral nerve stimulation would activate the hippocampus and hypothalamus structures which are affected in Alzheimer's disease (AD). This assumption is based upon animal experimental studies in which hippocampal activity was found to increase after peripheral tactile stimulation and the activity of the hypothalamus was enhanced by electro-acupuncture, a type of peripheral electrical stimulation. The hippocampus is highly involved in memory processes, in close association with other brain regions such as the inferomedial temporal cortex and the ventromedial prefrontal cortex. The hypothalamus plays a crucial role in affective behavior in Alzheimer's disease.

Most nerves in the human body are composed of thousands of fibers, of different sizes designated by groups A, B and C, which carry signals to and from the brain. The vagus nerve, for example, may have approximately 100,000 fibers of the three different types, each carrying signals. Each axon (fiber) of that nerve conducts only in one direction, in normal circumstances. The A and B fibers are myelinated (i.e., have a myelin sheath, constituting a substance largely composed of fat), whereas the C fibers are unmyelinated.

A commonly used nomenclature for peripheral nerve fibers, using Roman and Greek letters, is given in the table below,

| Group | External Diameter ($\mu$m) | Conduction Velocity (m/sec) |
|---|---|---|
| Myelinated Fibers | | |
| A$\alpha$ or IA | 12–20 | 70–120 |
| A$\beta$: IB | 10–15 | 60–80 |
| II | 5–15 | 30–80 |
| A$\gamma$ | 3–8 | 15–40 |
| A$\delta$ or III | 3–8 | 10–30 |
| B | 1–3 | 5–15 |
| Unmyelinted fibers | | |
| C or IV | 0.2–1.5 | 0.5–2.5 |

The diameters of group A and group B fibers include the thicknesses of the myelin sheaths. Group A is further subdivided into alpha, beta, gamma, and delta fibers in decreasing order of size. There is some overlapping of the diameters of the A, B, and C groups because physiological properties, especially the form of the action potential, are taken into consideration when defining the groups. The smallest fibers (group C) are unmyelinated and have the slowest conduction rate, whereas the myelinted fibers of group B and group A exhibit rates of conduction that progressively increase with diameter. Group B fibers are not present in the nerves of the limbs, they occur in white rami and some cranial nerves. Myelinated fibers also have very low stimulation thresholds compared to the unmyelinated type, and exhibit a particular strength-duration curve or respond to a specific pulse width versus amplitude for stimulation. The A and B fibers can be stimulated with relatively narrow pulse widths, from 50 to 200 microseconds ($\mu$s), for example. The A fiber conducts slightly faster than the B fiber and has a slightly lower threshold. The C fibers are very small, conduct electrical signals very slowly, and have high stimulation thresholds typically requiring a wider pulse width (300–1,000 $\mu$s) and a higher amplitude for activation. Selective stimulation of only A and B fibers is readily accomplished. The requirement of a larger and wider pulse to stimulate the C fibers, however, makes selective stimulation of only C fibers, to the exclusion of the A and B fibers, virtually, unachievable inasmuch as the large signal will tend to activate the A and B fibers to some extent as well.

A-Beta fibers respond very well to high frequency stimulation, e.g., 100 Hz with an intensity just above threshold. In a recent study, A-Beta fibers also appeared to respond to low-frequency stimulation (2 Hz) with a higher intensity. Activation of A-Delta and C fibers is usually caused by low-frequency stimulation (less than 10 Hz) with higher intensity. To activate all three types of afferent nerve fibers, high-frequency and low-frequency stimulation can be combined in one treatment.

The vagus nerve is composed of somatic and visceral afferents (i.e., inward conducting nerve fibers which convey impulses toward the brain) and efferents (i.e., outward conducting nerve fibers which convey impulses to an effector). Usually, nerve stimulation activates signals in both directions (bi-directionally). It is possible, however, through the use of special electrodes and waveforms, to selectively stimulate a nerve in one direction only (unidirectionally). The vast majority of vagal nerve fibers are C fibers, and a majority are visceral afferents having cell bodies lying in masses or ganglia in the skull. The central projections terminate largely in the nucleus of the solitary tract which sends fibers to various regions of the brain, e.g., the hypothalamus, hippocampus, and amygdala. See FIG. 1 (from: *Epilepsia*, vol. 31, suppl. 2: 1990, page S2).

An activation of higher-level areas, e.g. the hippocampus and hypothalamus, by TENS or cranial nerve (such as vagal nerve) stimulation might be transmitted by afferent nerve fibers, i.e. thick-myelinated A-Beta fibers, thin-myelinated A-Delta fibers, and Unmyelinated C fibers. The basic premise of vagal nerve stimulation is that vagal visceral afferents have a diffuse central nervous system (CNS) projection, and activation of these pathways has a widespread effect on neuronal excitability.

Observations on the profound effect of electrical stimulation of the vagus nerve on central nervous system (CNS) activity, extends back to 1930's. Intermittent vagal stimulation has been relatively safe and well tolerated. The minimal side effects of tingling sensations and brief voice abnormalities have not been distressing. The vagus nerve provides an easily accessible, peripheral route to modulate central nervous system (CNS) function. Other cranial nerves can be used for the same purpose, but the vagus nerve is preferred because of its easy accessibility. In the human body there are two vagal nerves (VN), the right VN and the left VN. Each vagus nerve is encased in the carotid sheath along with the carotid artery and jugular vein. The innervation of the right and left vagal nerves is different. The innervation of the right vagus nerve is such that stimulating it results in profound bradycardia (slowing of the heart rate). The left vagal nerve has some innervation to the heart, but mostly innervates the visceral organs such as the gastrointestinal tract. It is known that stimulation of the left vagal nerve does not cause any significant deleterious side effects.

The cervical component of the vagus nerve ($10^{th}$ cranial nerve) transmits primarily sensory information that is important in the regulation of autonomic activity by the parasympathetic system. General visceral afferents constitute approximately 80% of the fibers of the nerve, and thus it is not surprising that vagal stimulation (VS) can profoundly affect CNS activity. With cell bodies in the nodose ganglion, these afferents originate from receptors in the heart, aorta, lungs, and gastrointestinal system and project primarily to the nucleus of the solitary tract which extends throughout the length of the medulla oblongata U.S. Pat. No. 3,796,221 (Hagfors) is directed to controlling the amplitude, duration and frequency of electrical stimulation applied from an externally located transmitter to an implanted receiver by inductively coupling. Electrical circuitry is schematically illustrated for compensating for the variability in the amplitude of the electrical signal available to the receiver because of the shifting of the relative positions of the transmitter-receiver pair. By highlighting the difficulty of delivering consistent pulses, this patent points away from applications such as the current application, where consistent therapy may need to be continuously sustained over a prolonged period of time. The methodology disclosed is focused on circuitry within the receiver, which would not be sufficient when the transmitting coil and receiving coil assume significantly different orientation, which is likely in the current application. The present invention discloses a novel approach for this problem, using "targets" located in the external patch electrode. Additionally, the mode of stimulation in Hagfors patent is "bipolar" whereas in the current patent, the mode of stimulation is "unipolar" i.e. between the tip electrode and case.

U.S. Pat. No. 5,269,303 (Wernicke) is directed to the use of pacemaker technology (an implantable pulse generator) for the treatment of dementia. The pacemaker technology concept consists of a stimulating lead which is connected to a pulse generator (containing the circuity and DC power source) implanted subcutaneously or submuscularly, somewhere in the pectoral or axillary region, with a personal computer (PC) based programmer being external. Once the patient is programmed, the fully functional circuity and power source being fully implanted within the patients body. In such a system when the battery is depleted, the whole pulse generator (circuitry and power source) is disconnected from the permanently implanted lead and replaced in a surgical procedure. This patent neither anticipates practical problems of an inductively coupled system for adjunct therapy of dementia, nor suggest solutions to the same for an inductively coupled system for adjunct therapy of dementia.

U.S. Pat. No. 4,867,164 (Zabara) generally discloses animal research and experimentation related to epilepsy and the like, and use of pacemaker technology (an implantable pulse generator) for the stimulation of vagus nerve. Some of the key hypothesis on which the patent is based upon, have since been shown to be incorrect.

U.S. Pat. No. 5,540,734 (Zabara) is directed to stimulation of one or both of a patient's trigeminal and glossopharyngeal nerve utilizing an implanted pulse generator.

U.S. Pat. No. 5,031,618 (Mullett) discloses a position sensor for chronically implanted neuro stimulator for stimulating the spinal cord. The position sensor, located in a chronically implanted programmable spinal cord stimulator, modulates the stimulation signals depending on whether the patient is erect or supine.

U.S. Pat. No. 4,573,481 (Bullara) is directed to an implantable helical electrode assembly configured to fit around a nerve. The individual flexible ribbon electrodes are each partially embedded in a portion of the peripheral surface of a helically formed dielectric support matrix.

U.S. Pat. No. 3,760,812 (Timm et al.) discloses nerve stimulation electrodes that include a pair of parallel spaced apart helically wound conductors maintained in this configuration.

U.S. Pat. No. 4,979,511 (Terry) discloses a flexible, helical electrode structure with an improved connector for attaching the lead wires to the nerve bundle to minimize damage.

An implantable pulse generator and lead with a PC based external programmer is advantageous for cardiac pacing applications for several reasons, including:

1) A cardiac pacemaker needs to sense the intrinsic activity of the heart, because in vast majority of instances, the cardiac pacemakers deliver electrical output only during the brief periods when patients either have pauses in their intrinsic cardiac activity or during those periods of time when the heart rate drops (bradycardia) below a certain pre-programmed level. Therefore, for most of the time, in majority of patients, the cardiac pacemaker "sits" quietly monitoring the patient's intrinsic cardiac activity.

2) The stimulation frequency for cardiac pacing is typically close to 1 Hz as opposed to approximately 20 Hz or higher, typically used in nerve stimulation applications.

3) Majority of patients that require cardiac pacemaker support are typically in 60's, 70's or 80's years in age.

The combined effect of these three factors is that the pacemaker can have a battery life of 10–15 years, and for most patients in whom a pacemaker is indicated are implanted only once, with perhaps one surgical pulse generator replacement.

For nerve stimulation applications, the stimulation frequency is typically 20 Hz or higher, and the total stimulation time per day is much longer, which results in battery expenditure that is typically much higher than for cardiac pacemakers, and the battery will not last nearly as long. The impact of surgical generator replacement and expense will become significant, and detract from the appeal of this therapy. There are several other advantages of the present inductively coupled system as set forth below, 1) The hardware components implanted in the body are much less. This is advantageous for the patient in terms of patient comfort, and it decreases the chances of the hardware getting infected in the body. Typically, when an implantable system gets infected in the body, it cannot be easily treated with antibiotics and eventually the whole implanted system has to be explanted.
2) Because the power source is external, the physician can use stimulation sequences that are more effective and more demanding on the power supply such as longer "on" time.
3) The external inductively-coupled nerve stimulation (EINS) system is quicker and easier to implant.
4) The external pulse generator does not need to be monitored for "End-of-Life" EOL like the implantable system, thus resulting in cost saving and convenience.
5) The inductively-coupled nerve stimulation (EINS) system can be manufactured at a significantly lower cost than an implantable pulse generator and programmer system, providing the patient and medical establishment with cost effective therapies.
6) The EINS system makes it more convenient for the patient or caretaker to turn the device on.
7) Occasionally, an individual responds adversely to a medical device and the implanted hardware must be removed. In such a case, a patient having the EINS system has less implanted hardware to be removed and the cost of pulse generator does not become a factor.

In the conventional manner of implanting, a cervical incision is made above the clavicle, and another infraclavicular incision is made in the deltapectoral region for the implantable stimulus generator pocket. To tunnel the lead to the cervical incision, a shunt-passing tool is passed from the cervical incision to the generator pocket, where the electrode is attached to the shunt-passing tool and the electrode is then "pulled" back to the cervical incision for attachment to the nerve. This standard technique has the disadvantage that it is time consuming and it tends to create an open space in the subcutaneous tissue. Post surgically the body will fill up this space with serous fluid, which can be undesirable.

To make the subcutaneous tunneling simpler and to avoid possible complication, one form of the implantable lead body is designed with a hollow lumen to aid in implanting. In this embodiment, a special tunneling tool slides into a hollow lumen. After the cervical and infraclavicular incisions are made, the tunneling tool and lead are simply "pushed" to the cervical incision and the tunneling tool is pulled out. Since the tunneling tool is inside the lead, no extra subcutaneous space is created around the lead, as the lead is pushed. This promotes better healing post-surgically.

The apparatus and methods disclosed herein also may be appropriate for the treatment of other conditions, as disclosed in co-pending applications filed on Oct. 26, 1998, entitled APPARATUS AND METHOD FOR ADJUNCT (ADD-ON) THERAPY OF PARTIAL COMPLEX EPILEPSY, GENERALIZED EPILEPSY AND INVOLUNTARY MOVEMENT DISORDERS UTILIZING AN EXTERNAL STIMULATOR, now U.S. Pat. No. 6,205,359, and APPARATUS AND METHOD FOR ADJUNCT (ADD-ON) THERAPY FOR PAIN SYNDROMES UTILIZING AN IMPLANTABLE LEAD AND AN EXTERNAL STIMULATOR, now U.S. Pat. No. 6,208,902, the disclosures of which are incorporated herein by reference.

SUMMARY OF THE INVENTION

The apparatus and methodology of this invention generally relates to the treatment of Dementia including probable Alzheimer's disease via afferent stimulation using an implantable lead and a stimulator outside the body. In one embodiment of the invention, the apparatus consists of an easy to implant lead-receiver, an external stimulator containing controlling circuitry and power supply, and electrode containing coil for inductively coupling the external pulse generator to the implanted lead-receiver. A separately provided tunneling tool may be used as an aid for implanting the lead-receiver.

In another embodiment of the invention, the implantable lead-receiver is inductively coupled to the external stimulator via a patch electrode containing coil. One feature of this invention is to consistently deliver energy from an external coil to an internal coil in an ambulatory patient. A design of the external patch contains means for compensating for relative movement of the axis of the external and internal coils by deflecting the energy via targets located in the external patch.

Another feature of this invention is to provide an apparatus to aid in implanting the lead-receiver, including a hollow lumen in the lead body to receive a tunneling tool.

BRIEF DESCRIPTION OF THE DRAWINGS

For the purpose of illustrating the invention, there are shown in accompanying drawing forms which are presently preferred, it being understood that the invention is not intended to be limited to the precise arrangement and instrumentalities shown.

FIG. 6 is a diagram showing the implanted lead-receiver underneath the skin, also showing the relative position of the external coil FIG. 7 is a diagram showing the proximal end of the lead-receiver.

FIG. 10 is a diagram of a tunneling tool for aiding in the implantation of the lead-receiver.

FIG. 11 is a diagram of another tunneling tool for aiding in the implantation of the lead-receiver.

FIG. 21 is a diagram of an electrode containing steroid drug in a silicone collar at the base of electrode.

FIG. 22 is a diagram of an electrode with steroid drug coated on the surface of the electrode.

FIG. 23 is a diagram of cross sections of implantable lead-receiver body showing different lumens.

Figure 1:
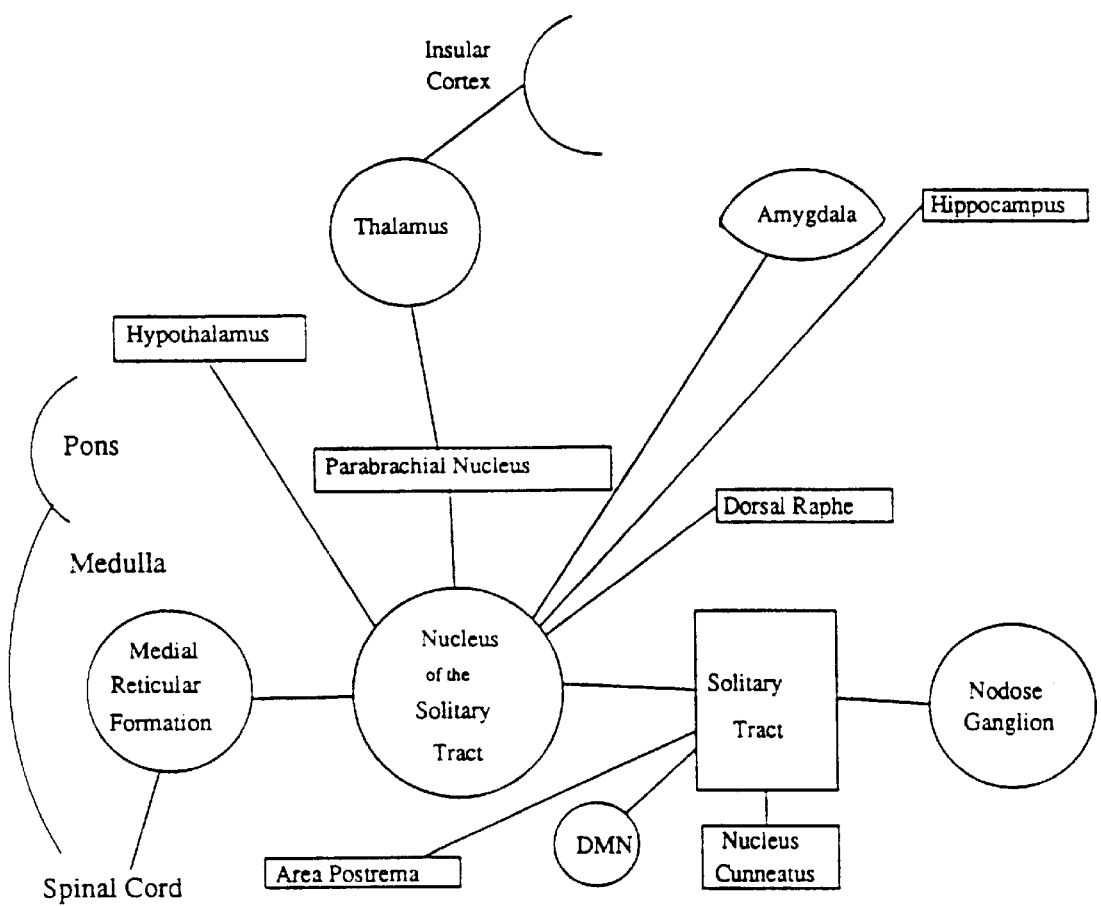
FIG. 1 is a diagram of vagal nerve afferents through the nucleus of the solitary tract.

The following are reference numbers in the drawing:

32. patient
34. implantable lead-receiver
36. coil-end of the external patch
38. wire of external patch
40. terminal end of the external patch
42. external stimulator
43. external patch electrode
44. belt of external stimulator
45. ferrite target
46. outer (transmitting) coil
48. inner (receiving) coil
49. proximal end of lead-receiver
50. adhesive portion of external patch electrode
51. driving voltage of transmitter coil
52. distal ball electrode
53. zero voltage of receiver coil
54. vagus nerve
55. signal voltage across receiver coil
56. carotid artery
57. ferrite targets in external patch
58. jugular vein
59. body of lead-receiver
60. working lumen of lead-receiver body
62. low lumen of lead-receiver body
64. schematic of lead-receiver circuitry
65. cable connecting cathode and anode
68. tuning capacitor in electrical schematic and in hybrid
70. zenor diode
71. pre-determined programs in block diagram
72. capacitor used in filtering
74. resister used in filtering
75. programmable control logic in block diagram
76. capacitor to block DC component to distal electrode
77. programming station in block diagram
78. case of lead-receiver
79. pulse frequency oscillator in block diagram
80. distal electrode in schematic of lead-receiver
81. battery (DC) in block diagram
82. working lumen in a cross section
83. amplifier in block diagram
84. hollow lumen in a cross-section
85. indicator in block diagram
86. small handle of alternate tunneling tool
87. low pass filter in block diagram
88. big handle of the tunneling tool
89. antenna in block diagram
90. skin
91. metal rod portion of the tunneling tool with big handle
92. punched holes in body of the lead receiver to promote fibrosis
93. metal rod portion of the alternative tunneling tool with small handle
94. alternative tunneling tool
95. tunneling tool with big handle
96. silicone covering proximal end
98. hybrid assembly
100. hydrogel
102. platinum electrodes around hydrogel
104. fiber electrode
105. spiral electrode
106. Dacron polyester or Polyimide
108. platinum fiber
110. exposed electrode portion of spiral electrode
112. polyurethane or silicone insulation in spiral electrode
114. "virtual" electrode
118. excitable tissue
120. non-excitable tissue
121. steroid plug inside an electrode
122. body of electrode
124. electrode tip
126. silicone collar containing steroid
128. steroid membrane coating
130. anchoring sleeve
132A–F lumens
134A–C larger hollow lumen for lead introduction

DETAILED DESCRIPTION OF THE INVENTION

Figure 1A:
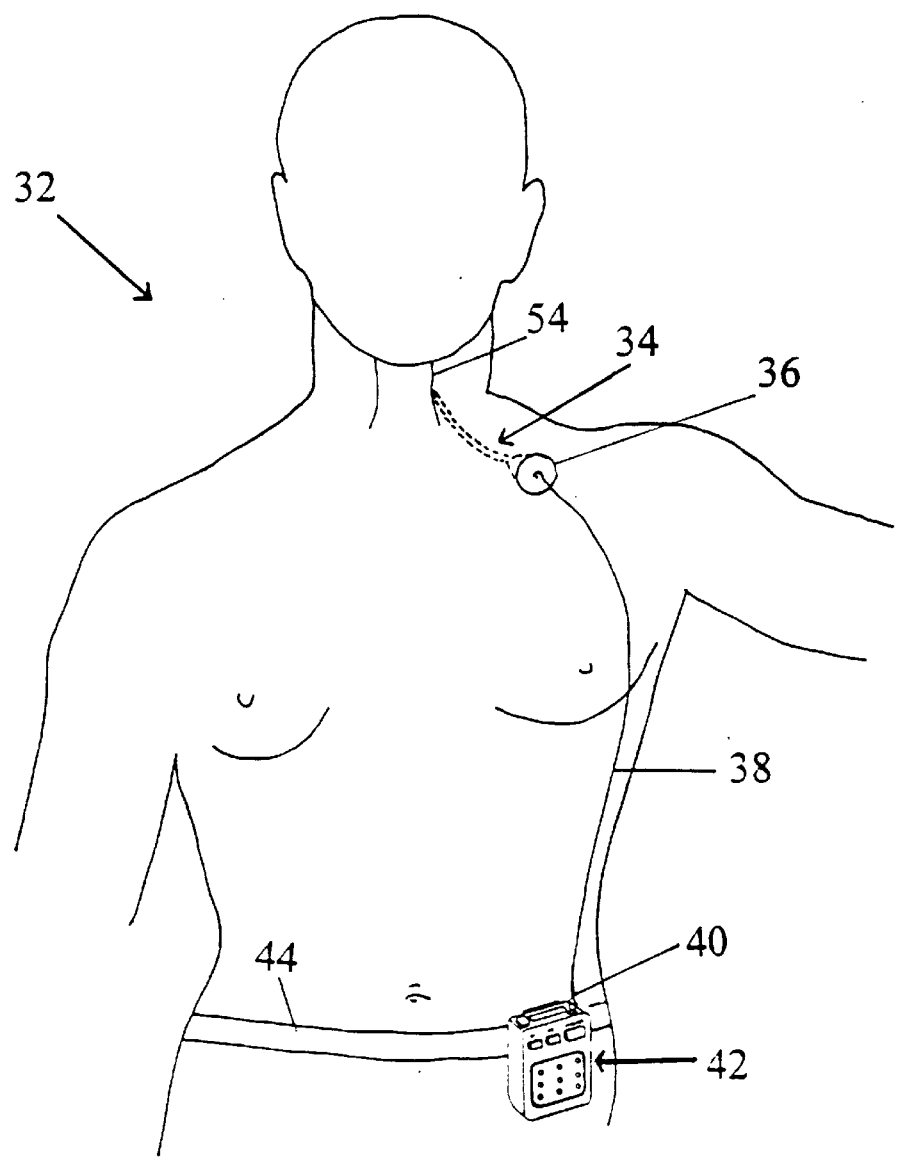
FIG. 1A is a diagram showing a patient wearing an external inductively-coupled nerve stimulator (EINS) system.

FIG. 1A shows a schematic diagram of a patient 32 with an implantable lead-receiver 34 and an external stimulator 42, clipped on to a belt 44 in this case. The external stimulator 42, may alternatively be placed in a pocket or other carrying device. An external patch electrode 36 provides the coupling between the external stimulator 42 and the implantable lead-receiver 34.

Figure 2:
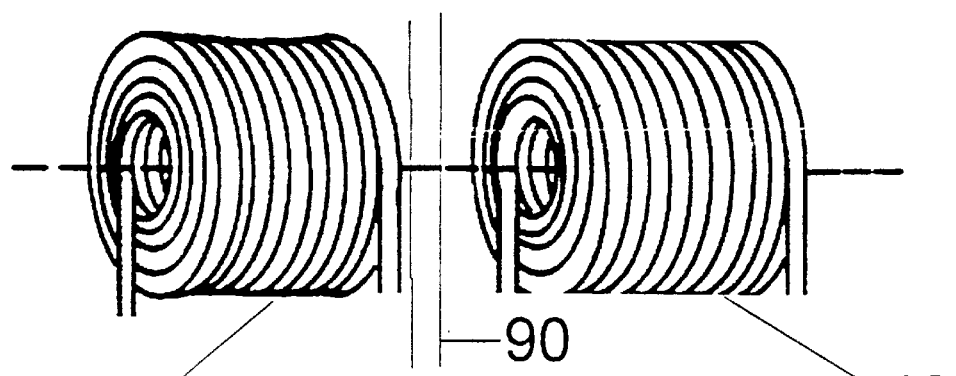
FIG. 2 is a diagram showing two coils along their axis, in a configuration such that the mutual inductance would be maximum.
Figure 5:
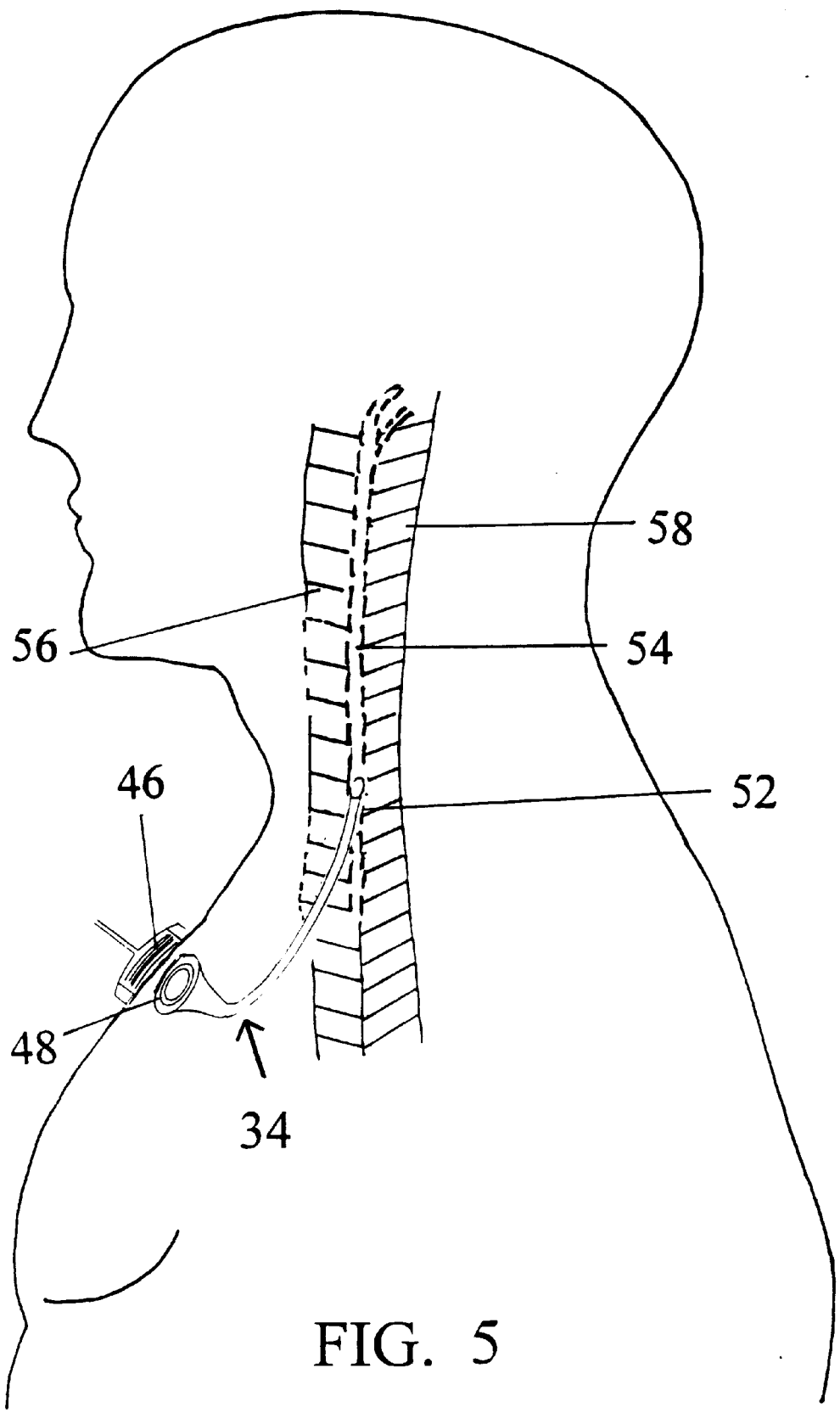
FIG. 5 is a diagram showing the implanted lead-receiver and the transmitting coil.

The external stimulator 42 is inductively coupled to the lead-receiver 34. As shown in FIG. 2, when two coils are arranged with their axes on the same line, current sent through coil 46 creates a magnetic field that cuts coil 48 which is placed subcutaneously. Consequently, a voltage will be induced in coil 48 whenever the field strength of coil 46 is changing. This induced voltage is similar to the voltage of self-induction but since it appears in the second coil because of current flowing in the first, it is a mutual effect and results from the mutual inductance between the two coils. Since these two coils are coupled, the degree of coupling depends upon the physical spacing between the coils and how they are placed with respect to each other. Maximum coupling exists when they have a common axis and are as close together as possible. The coupling is least when the coils are far apart or are placed so their axes are at right angles. As shown in FIG. 5, the coil 48 inside the lead-receiver 34 is approximately along the same axis as the coil 46 in the external skin patch 36.

Figure 3A:
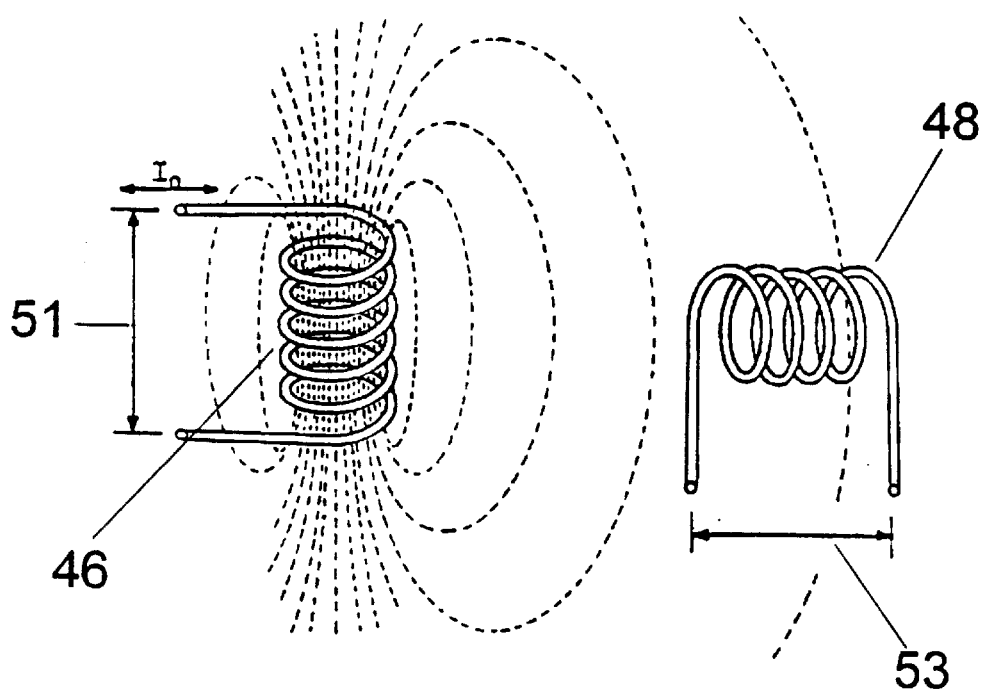
FIG. 3A is a diagram showing the effects of two coils with axes at right angles.
Figure 3B:
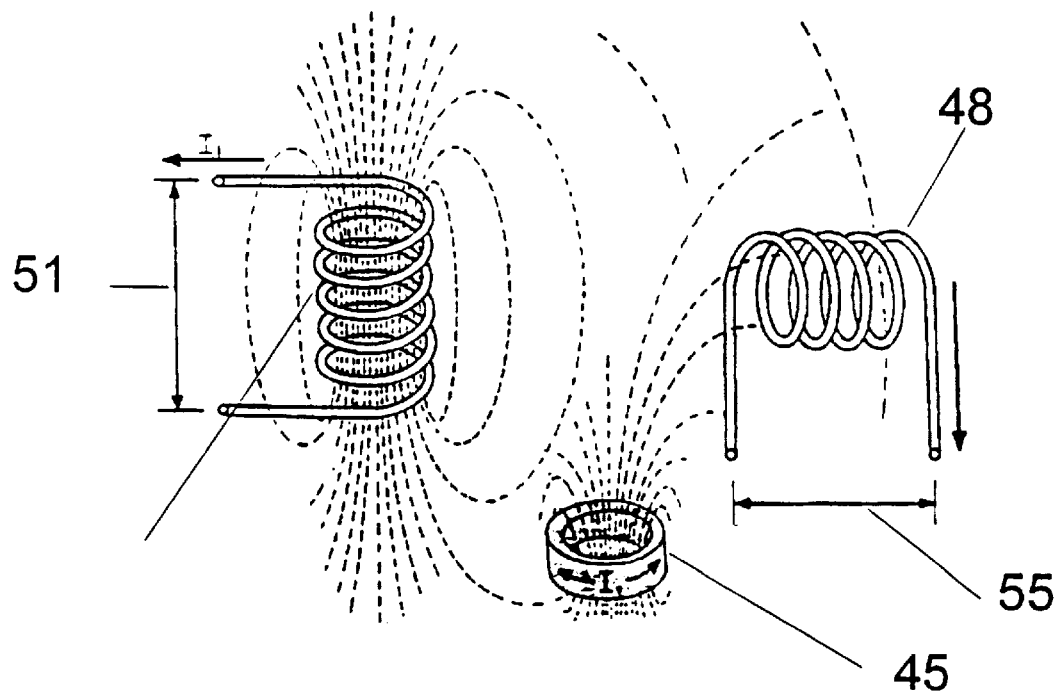
FIG. 3B is a diagram showing the effects of two coils with axes at right angles, with a ferrite target included.
Figure 4A:
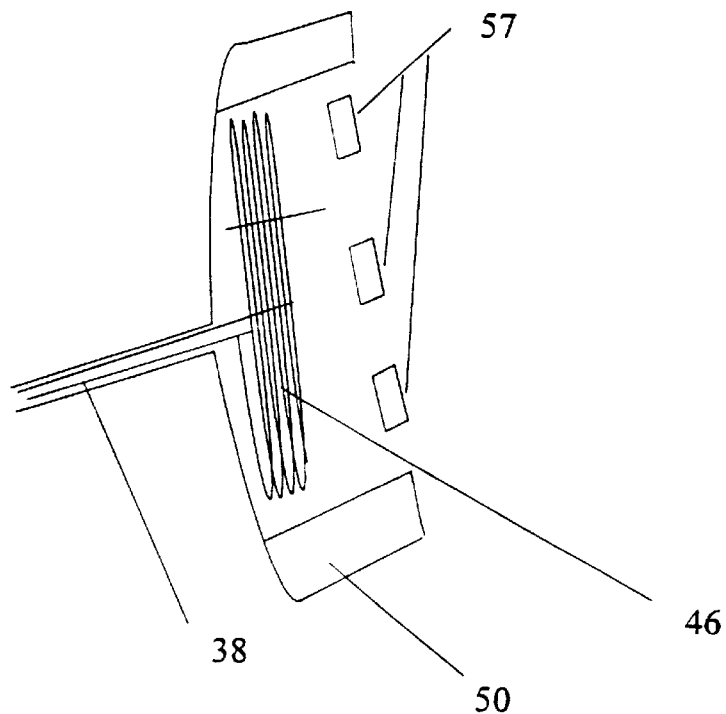
FIG. 4A is a side view of an external patch showing the transmitting coil and targets.
Figure 4B:
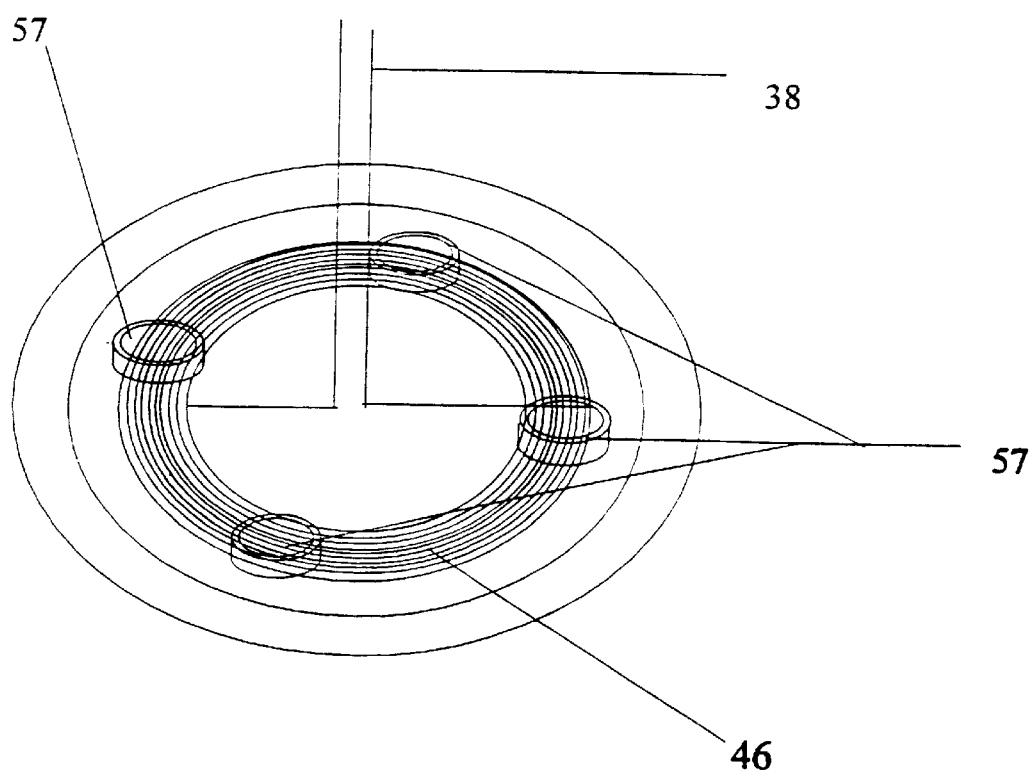
FIG. 4B is top view of an external patch showing the transmitting coil and targets.

As shown in FIG. 3A, when the axis of transmitting coil 46 is at right angles to the axis of the receiving coil 48, a given driving voltage 51 results in zero voltage 53 across the receiving coil 48. But, as shown in FIG. 3B by adding ferrite target 45, a given driving voltage 51 through the transmitting coil 46 results in a signal voltage 55 across the receiver coil 48. The efficiency is improved by having multiple ferrite targets. An alternate external patch shown in FIGS. 4A and 4B contains multiple targets 57. FIG. 4A shows a side view of the patch, and FIG. 4B shows a top view of the patch. Having multiple targets 57 in the external patch 43 compensates for non-alignment of the axis between the transmitting coil 46 and receiving coil 48. Since relative rotations between the axis of external transmitting coil 46 and internal receiving coil 48 which may occur during breathing, muscle contractions, or other artifacts are compensated for, results in continuous prolonged stimulation.

Figure 8:
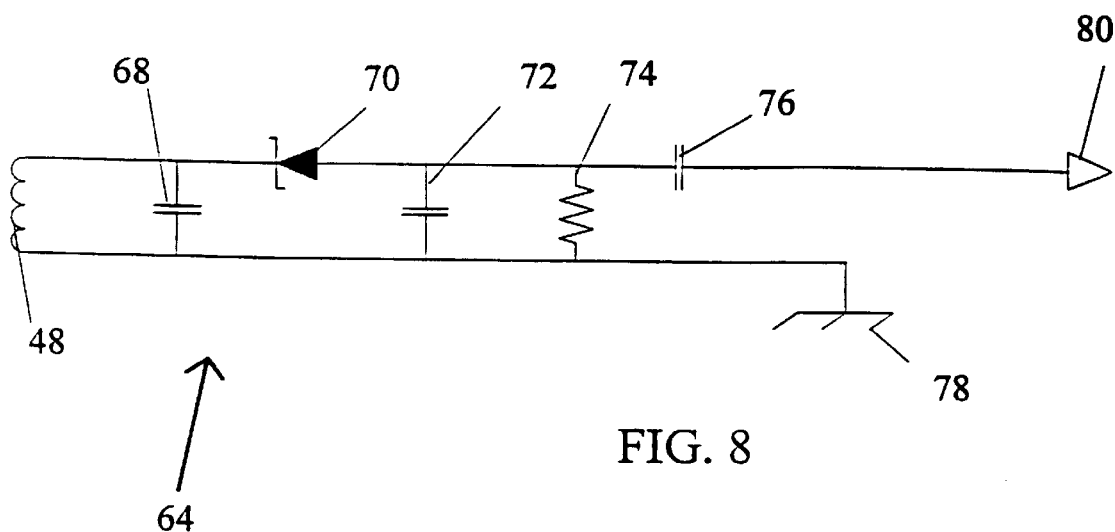
FIG. 8 is a diagram of circuitry within the proximal portion of the implanted lead-receiver.

Referring to FIG. 6, the implantable lead-receiver 34 looks somewhat like a golf "tee" and is the only implantable portion of the system. The "head" or proximal end 49 contains the coil 48 and electronic circuitry (hybrid) 98 which is hermetically sealed, and covered with silicone. It also has four anchoring sleeves 130 for tying it to subcutaneous tissue. FIG. 7 is a close-up view of the proximal portion 49 of the lead-receiver 34 containing the circuitry (hybrid) 98. This circuitry is shown schematically in FIG. 8. A coil 48 (preferably approximately 15 turns) is directly connected to the case 78. The external stimulator 42 and external patch 36 transmit the pulsed alternating magnetic field to receiver 64 whereat the stimulus pulses are detected by coil 48 and transmitted to the stimulus site (vagus nerve 54). When exposed to the magnetic field of transmitter 36, coil 48 converts the changing magnetic field into corresponding voltages with alternating polarity between the coil ends. A capacitor 68 is used to tune coil 48 to the high-frequency of the transmitter 36. The capacitor 68 increases the sensitivity and the selectivity of the receiver 64, which is made sensitive to frequencies near the resonant frequency of the tuned circuit and less sensitive to frequencies away from the resonant frequency. A zenor diode 70 in the current path is used for regulation and to allow the current that is produced by the alternating voltage of the coil to pass in one direction only. A capacitor 72 and resistor 74 filter-out the high-frequency component of the receiver signal and thereby leave a current of the same duration as the burst of the high-frequency signal. Capacitor 76 blocks any net direct current to the stimulating electrode tip 80, which is made of platinum/iridium (90%–10%). Alternatively, the stimulating electrode can be made of platinum or platinum/iridium in ratio's such as 80% Platinum and 20% Iridium.

The circuit components are soldered in a conventional manner to an upper conductive layer on a printed circuit board. The case 78 is connected to the coil 48 and is made of Titanium. The case 78 also serves as the return electrode (anode). The surface area of the anode exposed to the tissue is much greater than the surface area of the stimulating electrode 80 (cathode). Therefore, the current density at the anode is too low to unduly stimulate tissue that is in contact with the anode.

The body of the lead-receiver 34 is made of medical grade silicone (available from NuSil Technology, Applied silicone or Dow Chemical). Alternatively, the lead body 59 may be made of medical grade polyurethane (PU) of 55D or higher durometer, such as available from Dow Chemical. Polyurethane is a stiffer material than silicone. Even though silicone is a softer material, which is favorable, it is also a weaker material than PU. Therefore, silicone coated with Teflon (PTFE) is preferred for this application. PTFE coating is available from Alpa Flex, Indianapolis, Ind.

Figure 9:
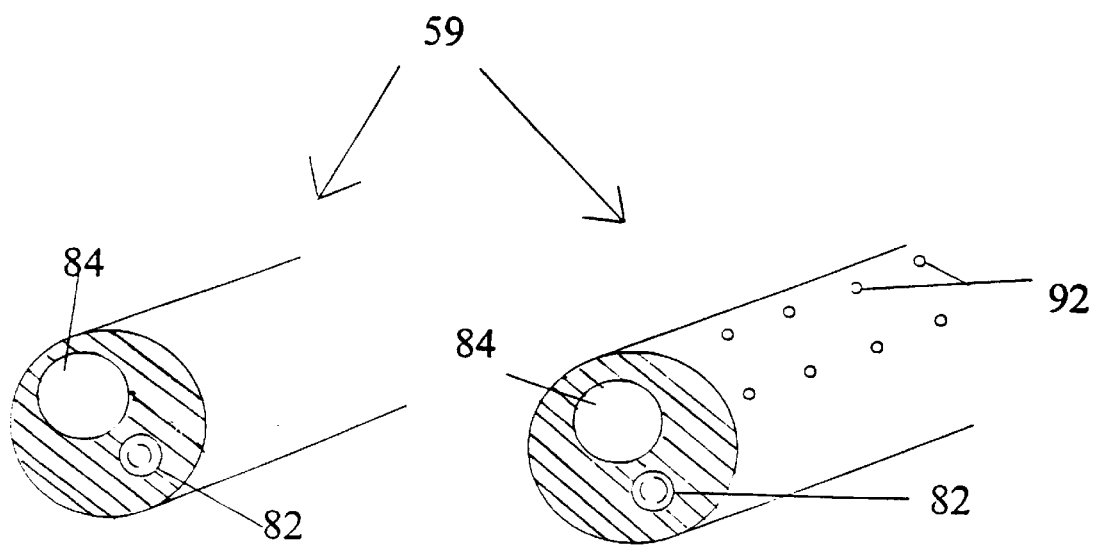
FIG. 9 is a diagram of the body of the lead-receiver.

FIG. 9 shows a close-up of the lead body 59 showing two lumens 82, 84. Lumen 82 is the "working" lumen, containing the cable conductor 65 which connects to the stimulating electrode 52. The other lumen 84 is preferably slightly larger and is for introducing and placing the lead in the body. Alternatively, lumen 84 may have small holes 92 punched along the length of the lead. These small holes 92 will promote fibrotic tissue in-growth to stabilize the lead position and inhibit the lead from migrating.

Silicone in general is not a very slippery material, having a high coefficient of friction. Therefore, a lubricious coating is added to the body of the lead. Such lubricous coating is available from Coating Technologies Inc. (Scotch Plains, N.J.). Since infection still remains a problem in a small percentage of patients, the lead may be coated with antimicrobial coating such as Silver Sulfer Dizene available from STS Biopolymers, Henrietta, N.Y. The lead may also be coated with anti-inflammatory coating.

The distal ball electrode 52, shown in FIG. 6 is made of platinum/iridium (90% platinum and 10% iridium). Platinum/iridium electrodes have a long history in cardiac pacing applications. During the distal assembly procedure, the silicone lead body 59 is first cleaned with alcohol. The conductor cable 65 (available from Lake Region, Minn.) is passed through the "working" lumen 82. The cable is inserted into the distal electrode 52, and part of the body of electrode is crimped to the cable 65 with a crimper. Alternatively, the cable conductor 65 may be arc welded or laser welded to the distal electrode 52. The distal end of the insulation is then slided over the crimp such that only the tissue stimulating portion of the distal electrode 52 is exposed. Following this, a small needle is attached to a syringe filled with medical glue. The needle is inserted into the distal end of insulation, and small amounts of medical glue are injected between the distal end of the insulation and distal electrode 52. The assembly is then cured in an oven.

As shown in FIGS. 9 and 10, a tunneling tool 95 is inserted into the empty lumen 84 to push the distal end (containing the cathode electrode 52) towards the vagus nerve 54. The tunneling tool 95, is comprised of a metal rod 91 and a handle 88. As shown in FIG. 11, another tunneling tool 94 with a smaller handle 86 may also be used. Both are available from Popper and Sons, New Hyde Park, N.Y. or Needle Technology. Alternatively, the tunneling tool may be made of strong plastic or other suitable material.

Figure 12:
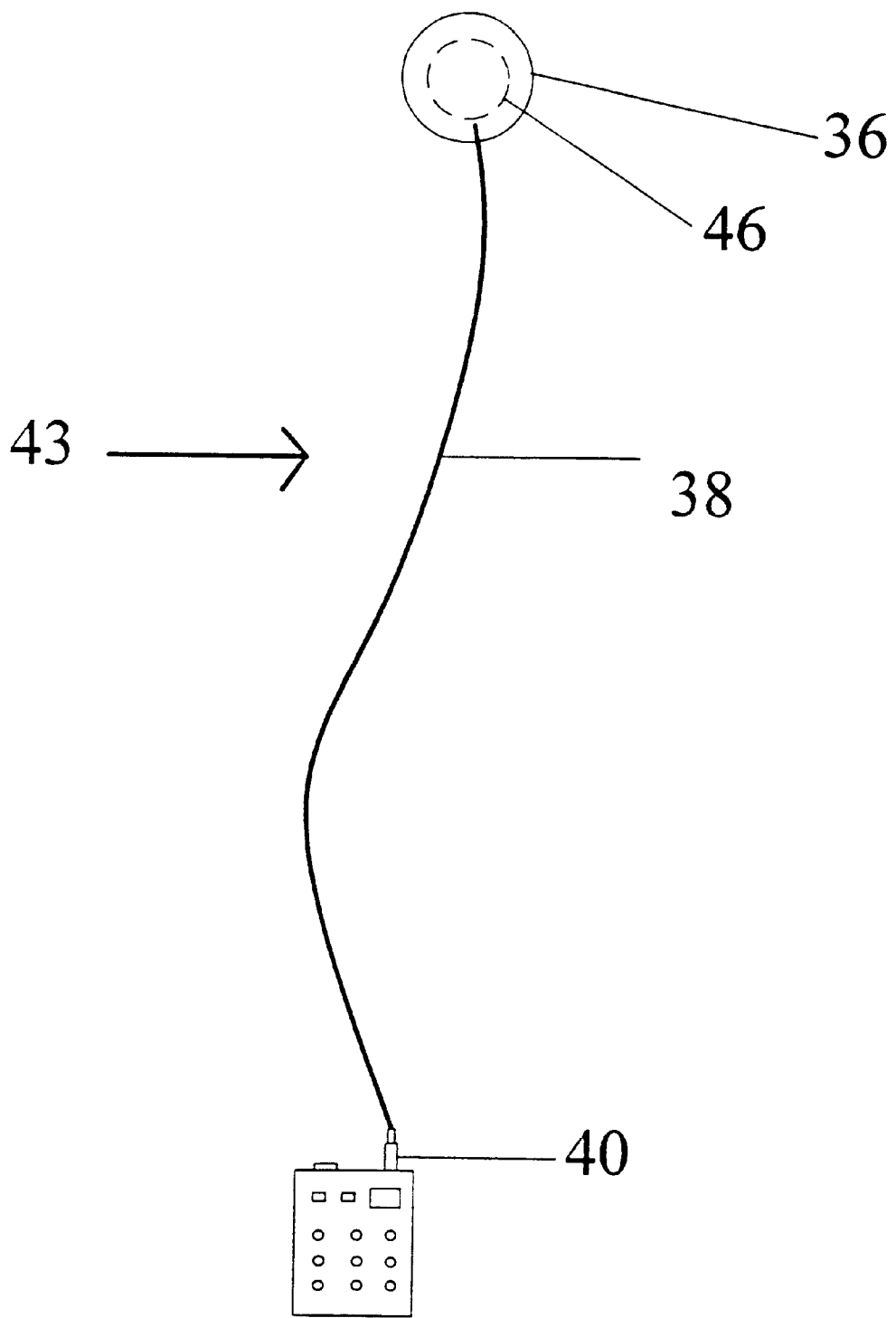
FIG. 12 is a diagram of an external patch and external pulse generator.

An external patch electrode 43 for inductive coupling is shown in FIG. 12. One end of the patch electrode contains the coil 46, and the other end has an adapter 40 to fit into the external stimulator 42. The external patch electrode 43, is a modification of the patch electrode available from TruMed Technologies, Burnsville, Minn.

Figure 13:
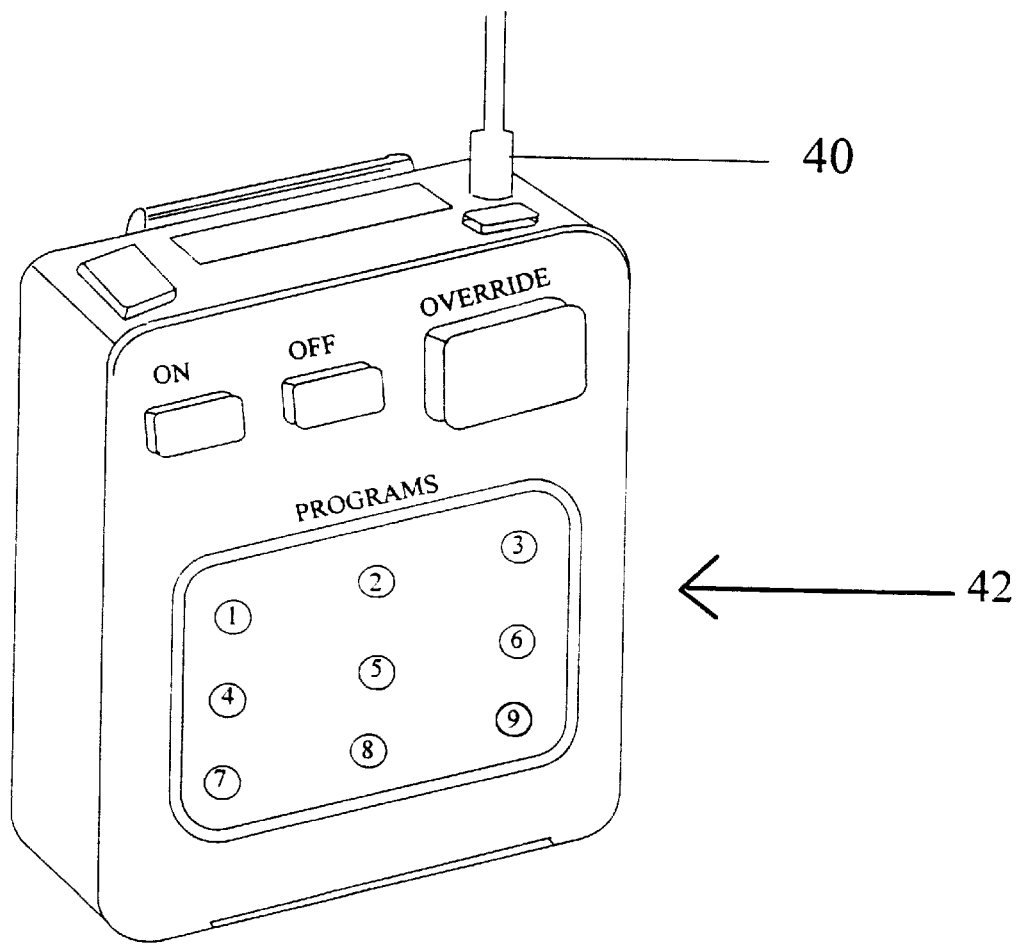
FIG. 13 is a prospective view of an external pulse generator.

FIG. 13 shows a sketch of the external stimulator 42, which preferably is slightly larger than a conventional pager. The external stimulator 42 contains the circuitry and rechargeable power source. There are several (approximately up to 9) pre-packaged programs, which differ in stimulus intensity, pulse width, frequency of stimulation, and on-off timing sequence, e.g. "on" for 10 seconds and "off" for 50 seconds in constant repeating cycles, for a given period of time. For patient safety any number of these programs may be locked-out by the manufacturer or physician. When the device is turned on, a green light emitting diode (LED) indicates that the device is emitting electrical stimulation. The following are examples of possible pre-determined programs.

Program #1: 2.5 mA constant current, 40 μs pulses, applied in bursts of trains, 10 pulses per train, with an internal frequency of 160 Hz, a repetition rate of 2 Hz applied for 30 minutes.

Program #2: 2.0 mA constant current, 40 μs pulses, applied in bursts of trains, 12 pulses per train, with an internal frequency of 160 Hz, a repetition rate of 2 Hz with ON time—10 sec and OFF time 10 sec, applied for 60 minutes.

Program #3: 3.0 mA constant current, 40 μs pulses, applied in bursts of trains, 8 pulses per train, with an internal frequency of 160 Hz, a repetition rate of 2 Hz with ON time 10 sec and OFF time 20 sec, applied for 120 minutes.

The above are examples of the pre-determined programs. The actual parameter settings for any given patient may deviate somewhat from the above.

Figure 14:
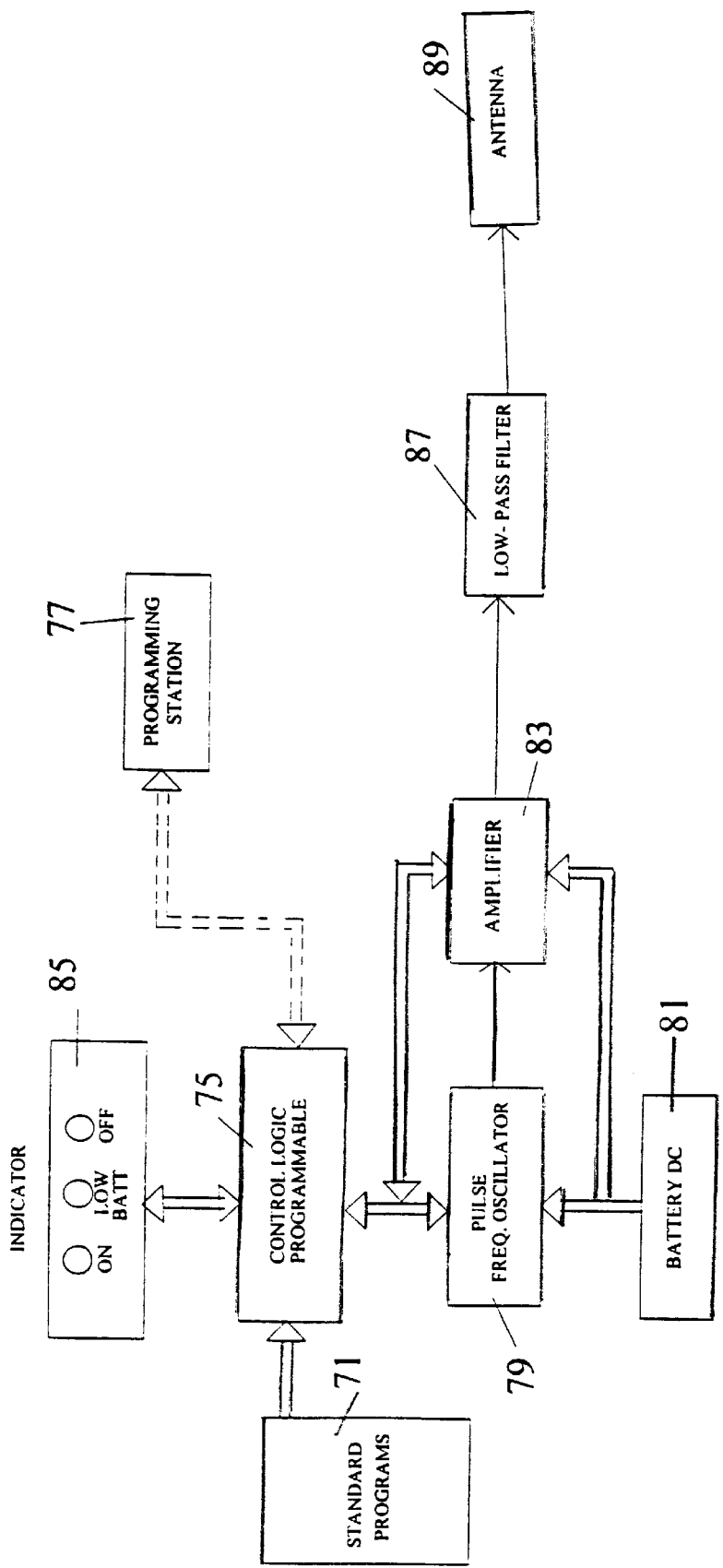
FIG. 14 is a flow diagram of the external pulse generator.

FIG. 14 is a top-level block diagram of the external stimulator 42. There are a series of (up to 9) pre-packaged programs 71, differing in the aggressiveness of the therapy. The standard programs feed into the programmable control logic 75. The programmable control logic 75 controls the pulse frequency oscillator 79 which sends appropriate pulses to the amplifier 83. From the amplifier 83, the signals go through a low pass filter 87 and to the antenna 89, which is then transmitted to the implanted lead-receiver for stimulation of the nerve. The programmable control logic 75 also feeds into an indicator 85 showing on-off status, as well as the battery status. The external stimulator 42 is powered by a DC battery 81. A programming station 77 provides the capability to download and change programs if the need arises.

Conventional integrated circuits are used for the logic, control and timing circuits. Conventional bipolar transistors are used in radio-frequency oscillator, pulse amplitude ramp control and power amplifier. A standard voltage regulator is used in low-voltage detector. The hardware and software to deliver these predetermined programs is well known to those skilled in the art.

The fabrication of the lead-receiver 34 is designed to be modular. Thus, several different components can be mixed and matched without altering the functionality of the device significantly. As shown in FIG. 6, the lead-receiver 34 components are the proximal end 49 (containing coil 48, electrical circuitry 98, and case 78), the lead body 59 containing the conductor 65, and the distal electrode (cathode) 52. In the modular design concept, several design variables are possible, as shown in the table below.

Table of lead-receiver design variables

| Proximal End Circuitry and Return electrode | Lead body-Lumens | Lead body-Insulation materials | Lead-Coating | Conductor (connecting proximal and distal ends) | Electrode - Material | Distal End Electrode - Type |
|---|---|---|---|---|---|---|
| | Single | Polyurethane | Lubricious (PVP) | Alloy of Nickal-Cobalt | Pure Platinum | Standard ball electrode |
| | Double | Silicone | Antimicrobial | | Platinum-Iridium (Pt/Ir) alloy | Hydrogel electrode |
| | Triple | Silicone with Polytetrafluoro ethylelne (PTFE) | Anti-inflammatory | | Pt/Ir coated with Titanium Nitride | Spiral electrode |
| | Coaxial | | | | Carbon | Steroid eluting Fiber electrode |

Either silicone or polyurethane is suitable material for this implantable lead body 59. Both materials have proven to have desirable qualities, which are not available in the other. Permanently implantable pacemaker leads made of polyurethane are susceptible to some forms of degradation over time. The identified mechanisms are Environmental Stress Cracking (ESC) and Metal Ion Oxidation (MIO). For this reason silicone material is slightly preferred over polyurethane.

Nerve-electrode interaction is an integral part of the stimulation system. As a practical benefit of modular design, any type of electrode described below can be used as the distal (cathode) stimulating electrode, without changing fabrication methodology or procedure significantly. When a standard ball electrode made of platinum or platinum/iridium is placed next to the nerve, and secured in place, it promotes an inflammatory response that leads to a thin fibrotic sheath around the electrode over a period of 1 to 6 weeks. This in turn leads to a stable position of electrode relative to the nerve, and a stable electrode-tissue interface, resulting in reliable stimulation of the nerve chronically without damaging the nerve.

Figure 15:
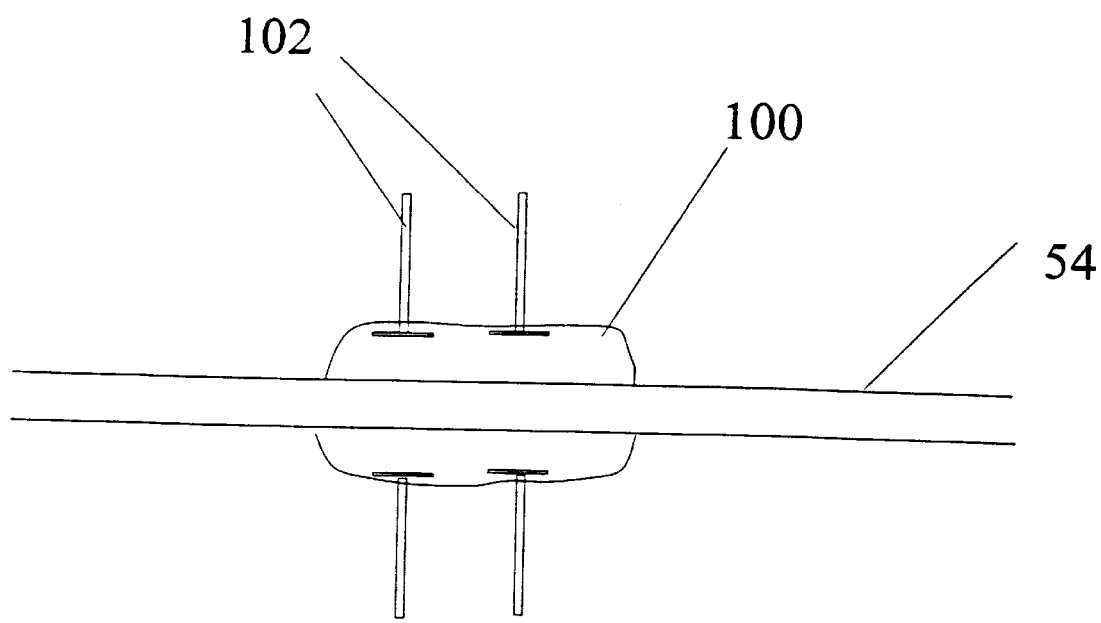
FIG. 15 is a diagram of a hydrogel electrode.

Alternatively, other electrode forms that are non-traumatic to the nerve such as hydrogel, platinum fiber, or steroid elution electrodes may be used with this system. The concept of hydrogel electrode for nerve stimulation is shown schematically in FIG. 15. The hydrogel material 100 is wrapped around the nerve 54, with tiny platinum electrodes 102 being pulled back from nerve. Over a period of time in the body, the hydrogel material 100 will undergo degradation and there will be fibrotic tissue buildup. Because of the softness of the hydrogel material 100, these electrodes are non-traumatic to the nerve.

Figure 16:
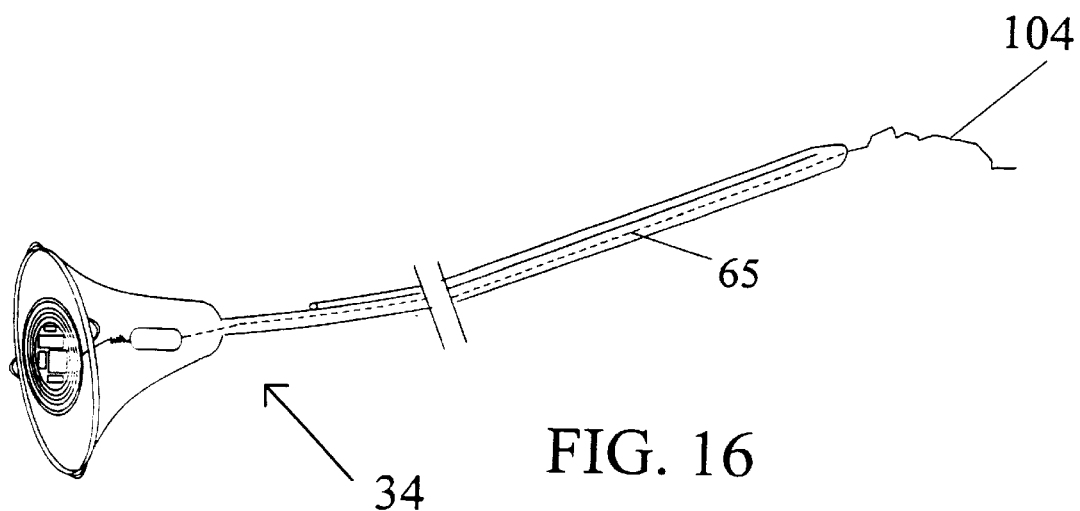
FIG. 16 is a diagram of a lead-receiver utilizing a fiber electrode at the distal end.
Figure 17:
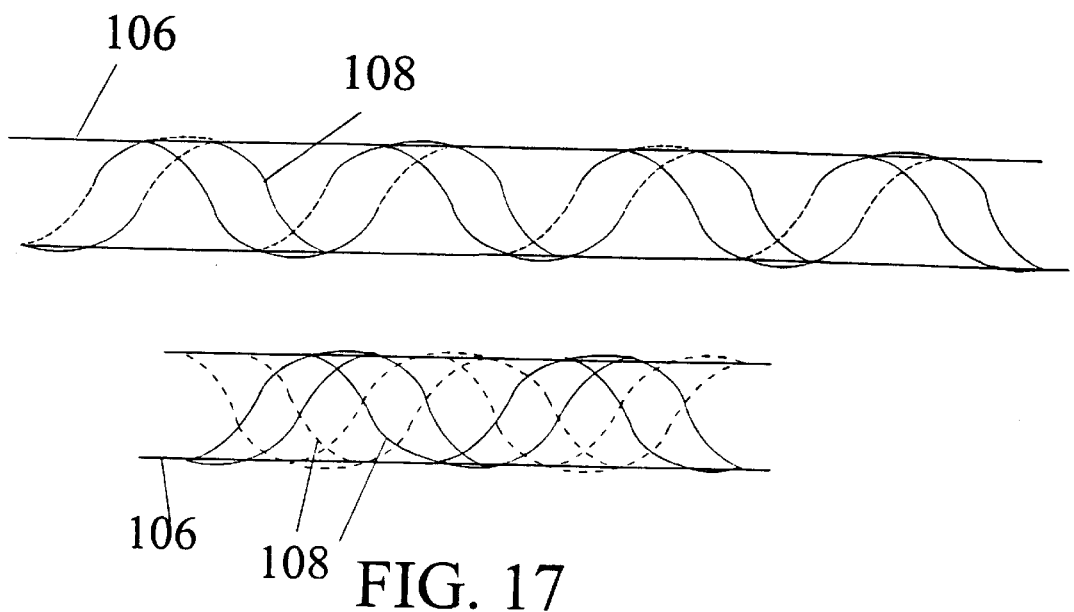
FIG. 17 is a diagram of a fiber electrode wrapped around Dacron polyester.
Figure 18:
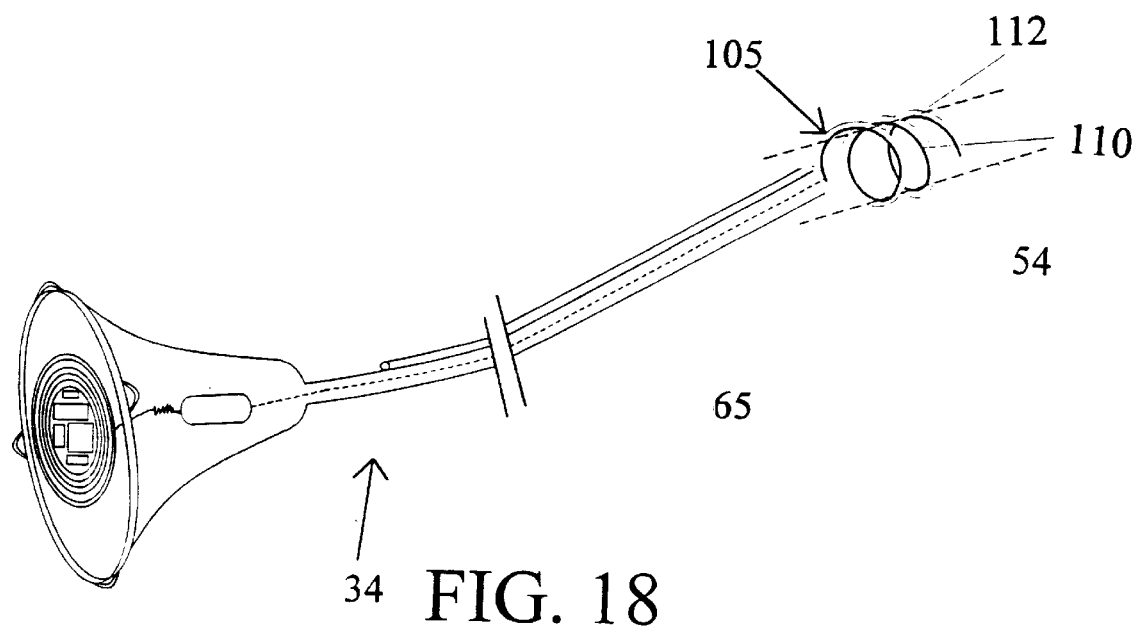
FIG. 18 is a diagram of a lead-receiver with a spiral electrode.

The concept of platinum fiber electrodes is shown schematically in FIG. 16. The distal fiber electrode 104 attached to the lead-receiver 34 may be platinum fiber or cable, or the electrode may be thin platinum fiber wrapped around Dacron polyester or Polyimide 106. As shown in FIG. 17, the platinum fibers 108 may be woven around Dacron polyester fiber 106 or platinum fibers 108 may be braided. At implant, the fiber electrode 104 is loosely wrapped around the surgically isolated nerve, then tied loosely so as not to constrict the nerve or put pressure on the nerve. As a further extension, the fiber electrode may be incorporated into a spiral electrode 105 as is shown schematically in FIG. 18. The fiber electrode 110 is on the inner side of polyurethane or silicone insulation 112 which is heat treated to retain its spiral shape.

Figure 19:
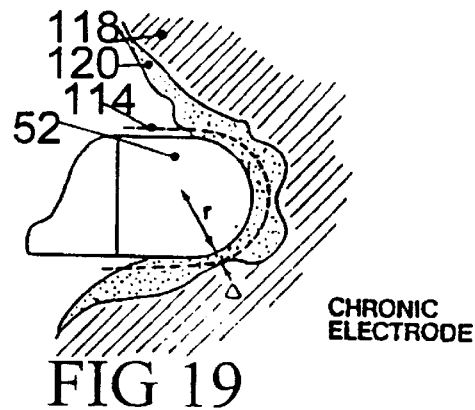
FIG. 19 is a diagram of an electrode embedded in tissue.

Alternatively, steroid elution electrodes may be used. After implantation of a lead in the body, during the first few weeks there is buildup of fibrotic tissue in-growth over the electrode and to some extent around the lead body. This fibrosis is the end result of body's inflammatory response process which begins soon after the device is implanted. The fibrotic tissue sheath has the net effect of increasing the distance between the stimulation electrode (cathode) and the excitable tissue, which is the vagal nerve in this case. This is shown schematically in FIG. 19, where electrode 52 when covered with fibrotic tissue becomes the "virtual" electrode 114. Non-excitable tissue is depicted as 120 and excitable tissue as 118. A small amount of corticosteroid, dexamethasone sodium phosphate commonly referred to as "steroid" or "dexamethasone" placed inside or around the electrode, has significant beneficial effect on the current or energy threshold, i.e. the amount of energy required to stimulate the excitable tissue. This is well known to those familiar in the art, as there is a long history of steroid elution leads in cardiac pacing application. It takes only about 1 mg of dexamethasone to produce the desirable effects. Three separate ways of delivering the steroid drug to the electrode nerve-tissue interface are being disclosed here. Dexamethasone can be placed inside an electrode with microholes, it can be placed adjacent to the electrode in a silicone collar, or it can be coated on the electrode itself.

Figure 20:
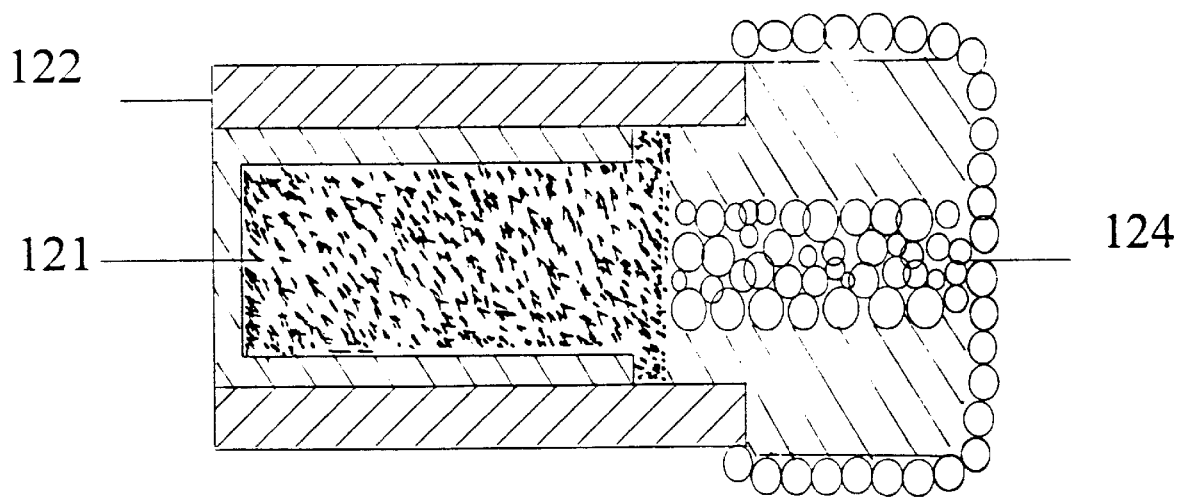
FIG. 20 is a diagram of an electrode containing steroid drug inside.

Dexamethasone inside the stimulating electrode is shown schematically in FIG. 20. A silicone core that is impregnated with a small quantity of dexamethasone 121, is incorporated inside the electrode. The electrode tip is depicted as 124 and electrode body as 122. Once the lead is implanted in the body, the steroid 121 elutes out through the small holes in the electrode. The steroid drug then has anti-inflammatory action at the electrode tissue interface, which leads to a much thinner fibrotic tissue capsule.

Another way of having a steroid eluting nerve stimulating electrode, is to have the steroid agent placed outside the distal electrode 52 in a silicone collar 126. This is shown schematically in FIG. 21. Approximately 1 mg of dexamethasone is contained in a silicone collar 126, at the base of the distal electrode 52. With such a method, the steroid drug elutes around the electrode 52 in a similar fashion and with similar pharmacokinetic properties, as with the steroid drug being inside the electrode.

Another method of steroid elution for nerve stimulation electrodes is by coating of steroid on the outside (exposed) surface area of the electrode. This is shown schematically in FIG. 22. Nafion is used as the coating matrix. Steroid membrane coating on the outside of the electrode is depicted as 128. The advantages of this method are that it can easily be applied to any electrode, fast and easy manufacturing, and it is cost effective. With this method, the rate of steroid delivery can be controlled by the level of sulfonation.

A schematic representation of the cross section of different possible lumens is shown in FIG. 23. The lead body 59 can have one, two, or three lumens for conducting cable, with or without a hollow lumen. In the cross sections, 132A–F represents lumens(s) for conducting cable and 134A–C represents hollow lumen for aid in implanting the lead.

Additionally, different classes of coating may be applied to the implantable lead-receiver 34 after fabrication. These coatings fall into three categories, lubricious coating, anti-microbial coating, and anti-inflammatory coating.

The advantage of modular fabrication is that with one technology platform, several derivative products or models can be manufactured. As a specific practical example, using a silicone lead body platform, three separate derivative or lead models can be manufactured by using three different electrodes such as standard electrode, steroid electrode or spiral electrode. This is made possible by designing the fabrication steps such that the distal electrodes are assembled at the end, and as long as the electrodes are mated to the insulation and conducting cable, the shape or type of electrode does not matter. Similarly, different models can be produced by taking a finished lead and then coating it with lubricious coating or antimicrobial coating. In fact, considering the design variables disclosed in table 1, a large number of combinations are possible. Of these large number of possible combinations, about 6 or 7 models are planned for manufacturing. These include lead body composed of silicone and PTFE with standard ball electrodes made of platinum/iridium alloy, and silicone lead body with spiral electrode.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A method to provide therapy for at least one of dementia or Alzheimer's disease comprising;
    a) providing an implantable lead-receiver comprising at least one electrode to stimulate a cranial nerve and a secondary coil electrically coupled to said at least one electrode;
    b) providing an external stimulator comprising circuitry to emit electrical signals, at least two predetermined programs to control said electrical signals, an external coil and a power supply;
    c) activating one of said at least two predetermined programs of said external stimulator to emit said electrical signals to said external coil;
    d) inductively transferring said electrical signals from said external coil of said external stimulator to said secondary coil of said lead-receiver;
    whereby said electrical signals stimulate said cranial nerve according to one of said at least two predetermined programs.

2. The method of claim 1, wherein said cranial nerve is the left vagus nerve.

3. The method of claim 1, wherein said lead receiver comprises a plurality of electrodes.

4. The method of claim 1, wherein the step of activating one of said at least two predetermined programs is manually performed.

5. The method of claim 1, further comprising manually controlling said electrical signals to stimulate said cranial nerve.

6. The method of claim 1, wherein
   a) said electrical signals comprise at least one variable component selected from the group consisting of the current amplitude, pulse width, frequency, and on-off timing sequence; and
   b) said at least two predetermined programs controls said variable component of said electrical signals.

7. The method of claim 1, further comprising manually disengaging said at least two predetermined programs.

8. The method of claim 1, wherein said at least two predetermined programs comprises at least three predetermined programs.

9. The method of claim 1, wherein said at least two predetermined programs comprises at least six predetermined programs.

10. The method of claim 1, wherein said at least two predetermined programs comprises approximately nine predetermined programs.

11. A method for providing therapy for the treatment of at least one of dementia or Alzheimer's disease comprising:
   a) selecting one of at least two predetermined programs to control the output of an external stimulator;
   b) activating said external stimulator to emit electrical signals in accordance with said one of at least two predetermined programs; and
   c) inductively coupling said external stimulator with an implantable lead-receiver to stimulate a cranial nerve.

12. The method of claim 11, further comprising implanting beneath the skin of a patient said lead-receiver in direct electrical contact with said cranial nerve.

13. The method of claim 11, wherein said predetermined programs comprises at least six predetermined programs.

14. A method to provide therapy for at least one of dementia or Alzheimer's disease comprising;
   a) providing an implantable lead-receiver comprising at least one electrode capable of providing a direct electrical contact with a cranial nerve and a secondary coil electrically coupled to said at least one electrode;
   b) providing an external stimulator comprising circuitry to emit electrical signals, at least three predetermined programs to control said electrical signals, an external coil and a power supply;
   c) activating one of said predetermined programs of said external stimulator to emit said electrical signals to said external coil;
   d) inductively transferring said electrical signals from said external coil of said external stimulator to said secondary coil of said lead-receiver;
   whereby said electrical signals stimulate said cranial nerve according to at least one of said predetermined programs.

15. The method of claim 14, wherein said predetermined programs comprises at least six predetermined programs.

16. The method of claim 14, wherein said predetermined programs comprises at least nine predetermined programs.

* * * * *